US00PP14824P2

(12) United States Plant Patent
Richards

(10) Patent No.: US PP14,824 P2
(45) Date of Patent: May 25, 2004

(54) TRADESCANTIA PLANT NAMED 'SATIN DOLL'

(50) Latin Name: *Tradescantia andersoniana*
Varietal Denomination: Satin Doll

(75) Inventor: Rod Richards, Farnham (GB)

(73) Assignee: Eternal Plant B.V., Boyl (NL)

( * ) Notice: Subject to any disclaimer, the term of this patent is extended or adjusted under 35 U.S.C. 154(b) by 0 days.

(21) Appl. No.: 10/628,761

(22) Filed: Jul. 28, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Tradescantia plant named 'Satin Doll', characterized by its upright and compact plant habit; rapid growth rate; freely and uniform flowering; and purple violet-colored flowers.

1 Drawing Sheet

Botanical classification/cultivar designation: *Tradescantia andersoniana* cultivar Satin Doll.

BACKGROUND OF THE INVENTION

The present Invention relates to a new and distinct cultivar of Tradescantia plant, botanically known as *Tradescantia andersoniana*, and hereinafter referred to by the name 'Satin Doll'.

The new Tradescantia is a product of a planned breeding program conducted by the Inventor in Churt, United Kingdom. The objective of the breeding program is to develop new compact and fast-growing Tradescantia cultivars.

The new Tradescantia originated from a pollination made by the Inventor in 1996 of two unidentified *Tradescantia andersoniana* selections, not patented. The new Tradescantia was discovered and selected as a single flowering plant by the Inventor in a controlled environment in Churt, United Kingdom in 1998 from the resultant progeny of the pollination. The new Tradescantia was selected on the basis of its compact plant habit, rapid growth rate and purple violet-colored flowers.

Asexual reproduction of the new cultivar by divisions taken at Churt, United Kingdom since 1998, has shown that the unique features of this new Tradescantia are stable and reproduced true to type in successive generations.

SUMMARY OF THE INVENTION

Plants of the cultivar Satin Doll have not been observed under all possible environmental conditions. The phenotype may vary somewhat with variations in environment such as temperature and light intensity without, however, any variance in genotype.

The following traits have been repeatedly observed and are determined to be the unique characteristics of 'Satin Doll'. These characteristics in combination distinguish 'Satin Doll' as a new and distinct Tradescantia cultivar:

1. Upright and compact plant habit.
2. Rapid growth rate.
3. Freely and uniform flowering habit.
4. Purple violet-colored flowers.

Plants of the new Tradescantia are most similar to plants of the parent selections. Plants of the new Tradescantia differ from plants of the parent selections and other Tradescantia cultivars known to the Inventor in leaf color, plant height and flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Tradescantia.

The photograph at the top of the sheet is a close-up view of a typical open flower, flower buds and leaves of 'Satin Doll'.

The photograph at the bottom of the sheet comprises a top perspective view of a typical plant of 'Satin Doll' grown in a ground bed.

DETAILED BOTANICAL DESCRIPTION

Plants shown in the aforementioned photographs and used in the following description were grown under conditions which closely approximate commercial production conditions during the spring in an outdoor nursery in 't Zand, The Netherlands. Plants were about one year old when the photographs and description were taken. During the production of the plants, day temperatures ranged from 5 to 20° C. and night temperatures ranged from 2 to 12° C. In the following description, color references are made to The Royal Horticultural Society Colour Chart, 1995 Edition, except where general terms of ordinary dictionary significance are used.

Botanical classification: *Tradescantia andersoniana* cultivar Satin Doll.

Parentage:

*Female, or seed, parent.*—Unidentified *Tradescantia andersoniana* selection, not patented.

*Male, or pollen, parent.*—Unidentified *Tradescantia andersoniana* selection, not patented.

Propagation:

*Type.*—By divisions.

*Time to initiate roots, summer.*—About 20 days at 21° C.

*Time to initiate roots, winter.*—About 30 days at 18° C.

*Root description.*—Fine.

Plant description:

*Form.*—Perennial. Upright and compact plant habit; inverted triangle. Flowering stems and leaves arise from the roots; moderately vigorous growth habit. Freely flowering with numerous flowers on numerous cincinni.

*Growth rate.*—Rapid; from divisions, about 15 weeks are required to produce fully-grown flowering plants in 15-cm containers.

*Plant height.*—About 24 cm.

*Plant width.*—About 20 cm.

*Stem description.*—Length: About 24 cm. Texture: Smooth, glabrous. Color: 146C with longitudinal stripes, 71A.

*Foliage description.*—Arrangement: Alternate, simple; sessile. Length: About 22 to 27 cm. Width: About 9 mm. Shape: Linear to lanceolate, ligulate. Apex: Mucronate. Base: Sheathed. Margin: Entire. Texture, upper and lower surfaces: Smooth, glabrous. Venation pattern: Parallel. Color: Developing and fully expanded foliage, upper surface: 144A; venation, 147A. Developing and fully expanded foliage, lower surface: 144A; venation, 147A.

Flower description:

*Flower arrangement and shape.*—Single flowers arranged in cincinni subtended by linear to lanceolate-shaped bracts. Freely and uniformly flowering habit; about 8 to 15 flowers and flower buds per plant.

*Natural flowering season.*—Continuous flowering during the late spring through the fall in The Netherlands.

*Flower longevity on the plant.*—Individual flowers last about three weeks on the plant. Flowers persistent.

*Fragrance.*—Not detected.

*Flower buds.*—Length: About 1 cm. Diameter: About 0.5 mm. Shape: Ovate. Color: 147C with longitudinal stripes, 186B.

*Flowers.*—Diameter: About 3 cm. Depth (height): About 8 mm.

*Petals.*—Quantity per flower: Three. Length: About 1.5 cm. Width: About 1.5 cm. Shape: Roughly orbicular. Apex: Obtuse to acute. Margin: Entire. Texture, upper and lower surfaces: Pubescent; glandular. Color: When opening and fully opened, upper surface: 81A. When opening and fully opened, lower surface: 82B.

*Sepals.*—Quantity per flower: Three. Calyx length: About 1 cm. Calyx width: About 4 mm. Shape: Ovate. Apex: Acute. Margin: Entire. Texture, upper and lower surfaces: Smooth, glabrous. Color, upper surface: 81A. Color, lower surface: 147C with longitudinal stripes, 186B.

*Pedicels.*—Length: About 1 cm. Diameter: About 1 mm. Color: 146C with longitudinal stripes, 71A.

*Reproductive organs.*—Stamens: Quantity per flower: Six. Anther attachment: Basifixed. Anther length: About 2 mm. Anther color: 16A. Pollen amount: Moderate. Pollen color: 16A. Pistils: Quantity per flower: One. Pistil length: About 7 mm. Stigma color: Creamy white. Style length: About 7 mm. Style color: 81A. Ovary color: 151A.

*Seed.*—Length: Less than 0.5 mm. Diameter: Less than 0.5 mm. Color: Light brown.

Disease/pest resistance: Plants of the new Tradescantia have not been noted to be resistant to pathogens and pests common to Tradescantia.

It is claimed:

1. A new and distinct cultivar of Tradescantia plant named 'Satin Doll', as illustrated and described.

* * * * *

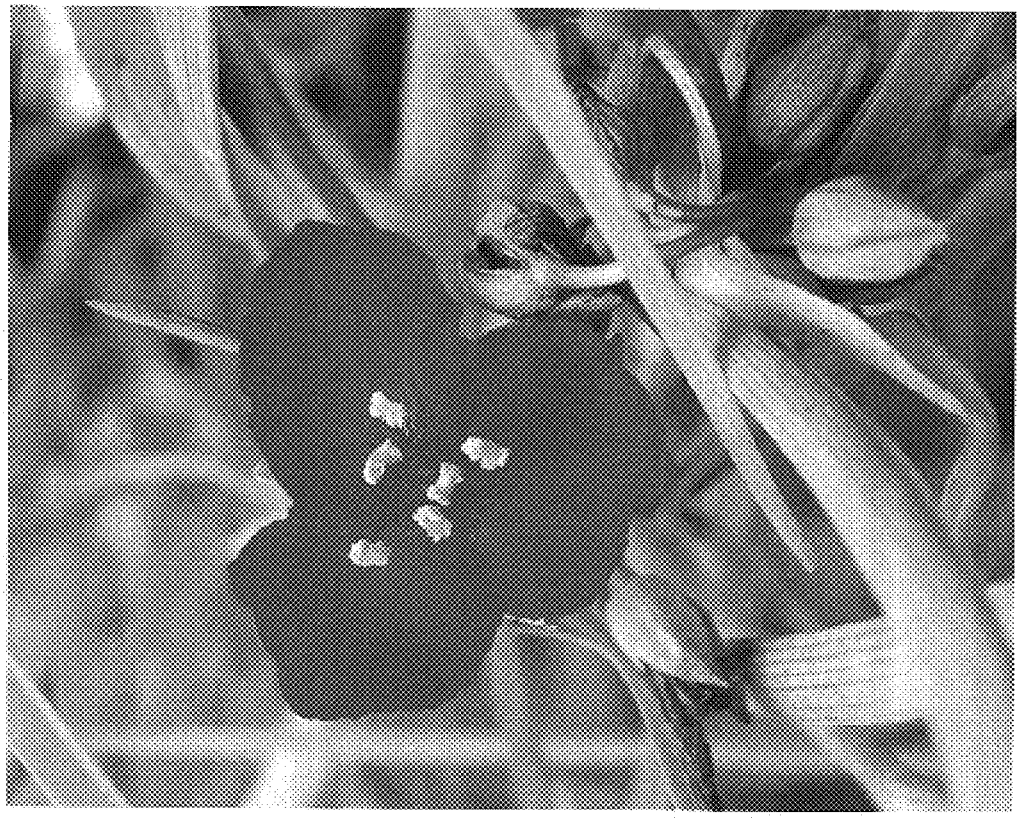
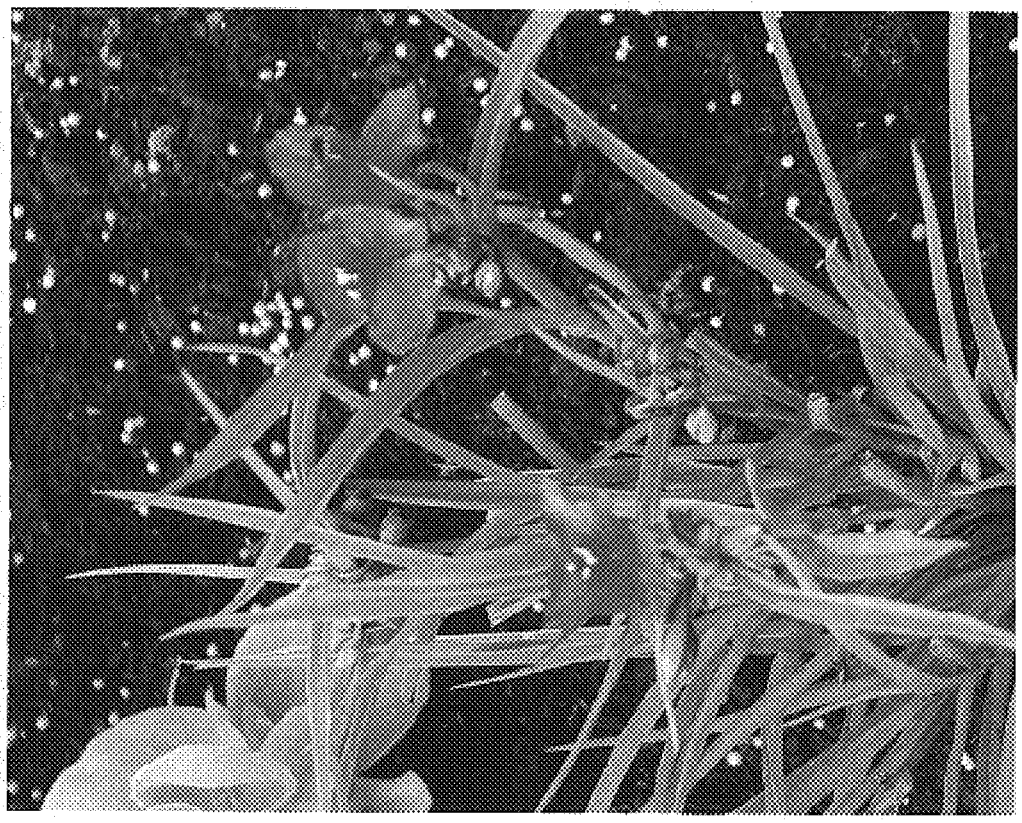
Tradescantia "Satin Doll"